United States Patent [19]
Frisch et al.

[11] Patent Number: 5,707,926
[45] Date of Patent: Jan. 13, 1998

[54] AQUEOUS DISPERSIONS OF SULFONYLUREA DERIVATIVES

[75] Inventors: Gerhard Frisch, Wehrheim/Taunus; Thomas Maier, Frankfurt am Main, both of Germany

[73] Assignee: Hoechst Aktiengesellschaft, Frankfurt, Germany

[21] Appl. No.: 692,254

[22] Filed: Aug. 5, 1996

Related U.S. Application Data

[63] Continuation of Ser. No. 450,372, May 25, 1995, Pat. No. 5,573,998, which is a continuation of Ser. No. 183,252, Jan. 19, 1994, abandoned, which is a continuation of Ser. No. 883,692, May 15, 1992, abandoned.

[30] Foreign Application Priority Data

May 18, 1991 [DE] Germany ............... 41 16 441.5

[51] Int. Cl.$^6$ ............... A01N 25/30; A01N 47/36
[52] U.S. Cl. ............... 504/116; 504/130; 504/211
[58] Field of Search ............... 504/116, 130, 504/211

[56] References Cited

U.S. PATENT DOCUMENTS

| | | | |
|---|---|---|---|
| 4,225,337 | 9/1980 | Levitt et al. | 71/92 |
| 4,483,781 | 11/1984 | Hartman et al. | 252/174.12 |
| 4,601,747 | 7/1986 | Willms | 71/92 |
| 4,718,937 | 1/1988 | Willms | 71/93 |
| 4,960,454 | 10/1990 | Borrod et al. | 71/92 |

FOREIGN PATENT DOCUMENTS

| | | |
|---|---|---|
| A-0 131 258 | 1/1985 | European Pat. Off. . |
| A-0 163 598 | 12/1985 | European Pat. Off. . |
| A-0 318 276 | 5/1989 | European Pat. Off. . |
| 0124295 | 3/1991 | European Pat. Off. . |
| A-0 420 497 | 4/1991 | European Pat. Off. . |
| WO 88/02598 | 4/1988 | WIPO . |

OTHER PUBLICATIONS

Mark H.F. et al.; *Encyclopedia of Polymer Science and Engineering, vol. 1: A to Amorphous Polymers*; J. Wiley & Sons, New York, 1985; pp. 211–231.

Primary Examiner—S. Mark Clardy
Attorney, Agent, or Firm—Curtis, Morris & Safford, P.C.

[57] ABSTRACT

Herbicidal active substances from the sulfonylurea series were hitherto mainly formulated as WPs or WGs. The invention relates to novel, storage-stable aqueous suspensions of these active substances, comprising a polyacrylic acid derivative, to processes for their preparation, and to their use in crop protection.

6 Claims, No Drawings

AQUEOUS DISPERSIONS OF SULFONYLUREA DERIVATIVES

This application is a continuation of application Ser. No. 08/450,372, filed May 25, 1995, now U.S. Pat. No. 5,573,998, which is a continuation of application Ser. No. 08/183,252, filed on Jan. 19, 1994 (now abandoned), which is a continuation of application Ser. No. 07/883,692, filed May 15, 1992 (now abandoned).

DESCRIPTION

The invention relates to aqueous preparations of sulfonylurea derivatives.

Active substances from the series of the sulfonylureas were hitherto formulated in particular as WPs (wettable powders) or WGs (water-dispersible granules).

The previous attempts to prepare aqueous suspensions of this substance class, where the active substance in a solid form, is finely dispersed in the aqueous phase, have proven difficult. One reason for this may lie in the fact that some of these compounds are very highly sensitive to hydrolysis. EP-A-124,295 discloses the preparation of useful aqueous formulations with suitable and compatible inorganic acid salts or certain carboxylic acid salts, in a pH range of 6–10. However, in doing this, exact concentration conditions and temperatures must be adhered to, which makes the procedure complicated.

Surprisingly, it has now been found that aqueous dispersions of the abovementioned active substances can be prepared in a simple manner with the aid of surfactants from the class of the polyacrylic acid derivatives. These formulations are extraordinarily storage-stable. For example, the aqueous formulations of amidosulfuron (3-(4,6-dimethoxypyrimidin-2-yl)-1-(N-methylsulfonyl)urea) are storage-stable over at least 3 months in a range from −10° C. to 40° C. and are not subject to chemical degradation. Storage at 50° C. over three months may result in a slight chemical degradation of the substance, without this endangering the stability of the suspension.

The surfactants mentioned protect the solid suspended active substance in such a manner that hydrolysis of the active substance is virtually completely prevented. They also exhibit their protective action when combined with one or more additional surfactants.

The invention therefore relates to aqueous herbicidal preparations which contain at least one herbicidal active substance from the series of the sulfonylureas and at least one polyacrylic acid derivative.

Suitable herbicides from the sulfonylurea series are pyrimidine- or triazinylaminocarbonyl-[benzene-, pyridine-, pyrazole-, thiophene- and (alkylsulfonyl)-alkylamino-] sulfamides. Preferred substituents on the pyrimidine ring or triazine ring are alkoxy, alkyl, haloalkoxy, haloalkyl, halogen or dimethylamino, it being possible for all substituents to be combined independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl and (alkanesulfonyl)alkylamino.

Examples of suitable sulfonylureas are

B1) phenyl- and benzylsulfonylureas and related compounds, for example 1-(2-chlorophenylsulfonyl)-3-(4-methoxy-6-methyl-1,3,5-triazin-2-yl)-urea (chlorsulfuron), 1-(2-ethoxycarbonylphenylsulfonyl)-3-(4-chloro-6-methoxypyrimidin-2-yl)-urea (chlorimuron-ethyl), 1-(2-methoxyphenylsulfonyl)-3-(4-methoxy-6-methyl-1,3,5-triazin-2-yl)-urea (metsulfuron-methyl), 1-(2-chloroethoxy-phenylsulfonyl)-3-(4-methoxy-6-methyl-1,3,5-triazin-2-yl)-urea (triasulfuron), 1(2-methoxycarbonyl-phenylsulfonyl)-3-(4,6-dimethylpyrimidin-2-yl)-urea (sulfometuron-methyl), 1-(2-methoxycarbonylphenylsulfonyl)-3-(4-methoxy-6-methyl-1,3,5-triazin-2-yl)-3-methylurea (tribenuron-methyl)

1-(2-methoxycarbonylbenzylsulfonyl)-3-(4,6-dimethoxypyrimidin-2-yl)-urea (bensulfuron-methyl)

1-(2-methoxycarbonylphenylsulfonyl)-3-(4,6-bis-(difluoromethoxy)-pyrimidin-2-yl)-urea (pyrimisulfuron-methyl)

3-(4-ethyl-6-methoxy-1,3,5-triazin-2-yl)-1-(2,3-dihydro-1,1-dioxo-2-methylbenzo[b]thiophene-7-sulfonyl)-urea (see EP-A-79,683) and 3-(4-ethoxy-6-ethyl-1,3,5-triazin-2-yl)-1-(2,3-dihydro-1,1-dioxo-2-methylbenzo[b]thiophene-7-sulfonyl)-urea (see EP-A-79,683), B2) thienylsulfonylureas, for example 1-(2-methoxycarbonylthiophen-3-yl)-3-(4-methoxy-6-methyl-1,3,5-triazin-2-yl)-urea (thifensulfuron-methyl), B3) pyrazolylsulfonylureas, for example 1-(4-ethoxycarbonyl-1-methylpyrazol-5-yl-sulfonyl)-3-(4,6-dimethoxypyrimidin-2-yl)-urea (pyrazosulfuron-methyl) and methyl 3-chloro-5-(4,6-dimethoxypyrimidin-2-ylcarbamoyl-sulfamoyl)-1-methyl-pyrazole-4-carboxylate (see EP-A-282,613), B4) sulfonediamide derivatives, for example 3-(4,6-dimethoxypyrimidin-2-yl)-1-(N-methyl-N-methylsulfonylaminosulfonyl)-urea (amidosulfuron) and structural analogs (see EP-A-0,131,258 and Z. Pfl. Krankh. Pfl. Schutz, Special Edition XII, 489–497 (1990)), B5) pyridylsulfonylureas, for example 1-(3-N,N-dimethylaminocarbonylpyridin-2-yl-sulfonyl)-3-(4,6-dimethoxypyrimidin-2-yl)-urea (nicosulfuron), 1-(3-ethylsulfonylpyridin-2-yl-sulfonyl)-3-(4,6-dimethoxypyrimidin-2-yl)-urea (DPX-E 9636, see Brighton Crop Prot. Conf.—Weeds—1989, p. 23 et seq.), pyridylsulfonylureas as are described in German Patent Applications P 4000503.8 (HOE 90/F 006) and P 4030577.5 (HOE 90/F 293), preferably those of the formula I or salts thereof,

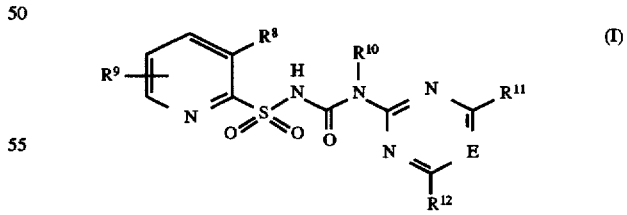

in which

E is CH or N, preferably CH, $R^6$ is iodine or $NR^{13}R^{14}$, $R^9$ is hydrogen, halogen, cyano, $(C_1–C_3)$-alkyl, $(C_1–C_3)$-alkoxy, $(C_1–C_3)$-haloalkyl, $(C_1–C_3)$-haloalkoxy, $(C_1–C_3)$-alkylmercapto, $(C_1–C_3)$-alkoxy-$(C_1–C_3)$-alkyl, $(C_1–C_3)$-alkoxy-carbonyl, mono- or di-$(C_1–C_3)$-alkyl-amino, $(C_1–C_3)$-alkyl-sulfinyl or -sulfonyl, $SO_2—NR^aR^b$ or $CO—NR^aR^b$, in particular H, $R^a$ and $R^b$ independently of one another are hydrogen, $(C_1-C_3)$-alkyl, $(C_1-C_3)$-alkenyl, $(C_1-C_3)$-alkynyl, or together are —$(CH_2)_4$—, —$(CH_2)_5$— or $(CH_2)_2$—O—$(CH_2)_2$—, $R^{10}$ is H or $CH_3$, $R^{11}$ is halogen, $(C_1-C_2)$-alkyl, $(C_1-C_2)$-alkoxy, $(C_1-C_2)$-haloalkyl, preferably $CF_3$, $(C_1-C_2)$-haloalkoxy, preferably $OCHF_2$ or $OCH_2CF_3$, $R^{12}$ is $(C_1-C_2)$-alkyl, $(C_1-C_2)$-haloalkoxy, preferably $OCHF_2$, or $(C_1-C_2)$-alkoxy, and $R^{13}$ is $(C_1-C_4)$alkyl and $R^{14}$ is $(C_1-C_4)$-alkylsulfonyl, or $R^{13}$ and $R^{14}$ together are a chain of the formula —$(CH_2)_3SO_2$— or —$(CH_2)_4SO_2$—, for example 3-(4,6-dimethoxypyrimidin-2-yl)-1-(3-N-methylsulfonyl-N-methylaminopyridin-2-yl)-sulfonylurea, B6) alkoxyphenoxysulfonylureas as are described in EP-A-0,342,569, preferably those of the formula II or salts thereof,

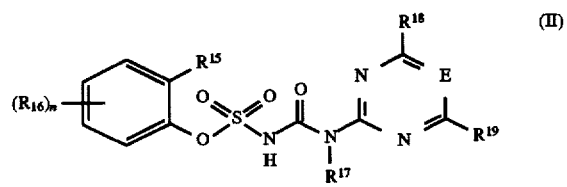

in which

E is CH or N, preferably CH, $R^{15}$ is ethoxy, propoxy or isopropoxy, $R^{16}$ is hydrogen, halogen, nitro, $CF_3$, CN, $(C_1-C_4)$-alkyl, $(C_1-C_4)$-alkoxy, $(C_1-C_4)$-alkylmercapto or $(C_1-C_3)$-alkoxy-carbonyl, preferably in the 6-position on the phenyl ring, n is 1, 2 or 3, preferably 1, $R^{17}$ is hydrogen, $(C_1-C_4)$-alkyl or $(C_3-C_4)$-alkenyl, $R^{18}$ and $R^{19}$ independently of one another are halogen, $(C_1-C_2)$-alkyl, $(C_1-C_2)$-alkoxy, $(C_1-C_2)$-haloalkyl $(C_1-C_2)$-haloalkoxy or $(C_1-C_2)$-alkoxy-$(C_1-C_2)$-alkyl preferably $OCH_3$ or $CH_3$, for example 3-(4,6-dimethoxy-pyrimidin-2 -yl)-1-(2-ethoxyphenoxy)-sulfonylurea, and other related sulfonylurea derivatives, and their mixtures.

The content of sulfonylurea derivatives, preferably sulfonediamide derivatives such as amidosulfuron, is preferably 0.1–60% by weight, in particular 1–45% by weight.

Suitable surfactants are in particular those polyacrylic acid derivatives as are available, for example, under the trade names ®Sokalan CP10 (BASF), the ®Geropon series (HB, DA, DG) (Rhone Poulenc) or ®Dispersant series (Rhone Poulenc) or the ®Degapas series (Degussa).

®Sokalan CP10 is a modified low molecular weight sodium polyacrylate which is prepared by a specific polymerization process (BASF Techn. Info TI/P 3039d, 1988.)

The ®Geropon types HB, DA and DG and ®Dispersant HB and FB are, according to Rhone-Poulenc Data Sheets of 1979 and 1989 respectively, alkali metal polyacrylates which are available both in liquid and in solid form.

The ®Degapas series also consists of alkali metal salts, or ammonium salts, of polyacrylic acid derivatives.

These polyacrylic acid derivatives can preferably be employed in a range from 0.1–30% by weight, but, in particular, from 0.5–20% by weight.

As an additional surfactant which helps improve the dispersing properties of the solid suspended particles, but which is not essential, the preparations according to the invention may contain a dodecyl- or tridecyl-benzenesulfonate in amounts of 0.01–12% by weight. For example, ®Maranil (sodium dodecylbenzenesulfonate), manufactured by Henkel, can be employed as a paste or a powder.

It is furthermore also possible to add up to 25% by weight, preferably up to 15% by weight, of commercially available adjuvants such as wetting agents, dispersants, defoamers, thickeners, preservatives and antifreeze agents.

Suitable additional wetting agents and dispersants are, for example, tributylphenol polyglycol ethers, such as the ®Sapogenat T brands (Hoechst) or nonylphenol polyglycol ethers, such as the ®Arkopal N brands (Hoechst).

Examples of suitable defoamers are those based on silicone, such as those from the ®Silcolapse series (Rhone Poulenc) or Antischaummittel SH (Wacker).

Thickeners can be of inorganic or organic nature; they can also be combined. Suitable examples are those based on aluminum, xanthan, methylcellulose, polysaccharide, alkaline earth metal silicate, gelatine and polyvinyl alcohol such as, for example, ®Bentone EW, ®Veegum, ®Rhodopol 23 or ®Kelzan S. If necessary, preservatives can be used, for example those based on formaldehyde, benzoic acid and triphenyltin such as, for example, ®Kobate C.

It is furthermore also possible to add antifreeze agents such as urea, salts, polyols (for example glycol, propylene glycol or glycerol) or sugars.

The invention furthermore relates to a method of controlling undesired vegetation, which comprises applying a preparation according to the invention to plants, seeds of plants or the area under cultivation.

The Examples 1–22 which follow (Table 1) are intended to illustrate the herbicidal preparations according to the invention without restricting the invention thereto. The suspensions are prepared by wet grinding in a manner conventionally used by those skilled in the art (quantities are in percent by weight). The degradation rates are given in the lower part of the tables.

Examples 18 and 19 are mixed formulations of isoproturon and amidosulfuron which, at an initial value of 1.5%, contain 1.47 and 1.46%, respectively, of amidosulfuron after 5 months at room temperature (RT), and the content after 3 months at 40° C. is 1.40 and 1.42%, respectively. Example 20 is a mixture of a commercially available ®Arelon dispersion (DE-A-2,924,403) and an amidosulfuron dispersion content according to Example 2 in Table 1. 81.7% of ®Arelon dispersion, 6% of amidosulfuron dispersion (Example 2) and 12.3% of water were mixed thoroughly, and the mixture was stored. Degradation after 3 months at 40° C. is 1.11%, and after 3 months at 50° C. the content is <0.1%, while 0.4 and 0.49%, respectively, were still detectable in Examples 18 and 19 after 3 months at 50° C.

Besides the possibility of preparing a stable aqueous formulation of sulfonylureas in the manner described herein, it is also possible to prepare mixed formulations of sulfonylureas with other biologically active substances in the same manner. This makes sense in particular if an addition of one or more further active substances can result in a broadened biological spectrum of action, or even lead to synergism. Mainly suitable here are herbicidally active substances such as phenylurea derivatives known under the common names (Pesticides Manual) isoproturon, linuron, monolinuron, monuron, diuron, neburon, chlortoluron, fluometuron, chlorbromuron, chloroxuron, fenuron, siduron, terbuthiuron, tetrafluron and metoxuron.

Further substances which are to be mentioned are those from the class of the triazines such as tributylazin, terbutryn, simetryn, simazine, secbumeton, propazine, prometryn, procyazine, metribuzin, cyprazine, cyanazin, atrazine, prometon, hexazinone, amitrol, dipropetryn, desmetryn and ametryn. The following are furthermore suitable: pendimethalin, trifluralin, CMPP, MCPA, 2, 4, D, glufosinate, glyphosate, nitrofen, bifenox, diclofop, ioxynil, bromoxynil, paraquat, ethalfluralin, ethofumesate, diflufenican, metolachlor, alachlor, acifluorfen, methalpropalin, nitralin, nitrofluorfen, fluoroglycofen, oxyfluorfen, profluralin, propachlor, 2,4-DB, 2,4-DP and bentazone.

These formulations can be formulated in the form of pure mixed dispersions and in the form of suspoemulsions as are described, for example, in EP-A-117,999 and EP-A-261,492.

These examples demonstrate that the dispersion in Example 1a was virtually stable from the physical point of view, but chemical degradation by 21.4% occurred after 3 months' storage at 50° C. resulting in a content of 27.5 %. Example 5a was not suitable for grinding. Example 3a was unstable from the physical point of view after one month and degradation resulted in a content of 39.9%; similarly Example 6a, where degradation resulted in 37.2%. Example 4a was unstable after 2 months, and degradation resulted in 37.7%. Equally, Example 2a is unstable after one month at 50° C. and degradation resulted in a content of 38.8%.

TABLE 1

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| Amido-sulfuron | 25 | 25 | 25 | 25 | 25 | 25 | 25 | 25 | 25 | 25 | 25 | 25 | 25 | 25 | 25 | 45 | 30 | 1.55 | 1.55 | *) | 25 | 25 |
| ® Sokalan CP10 |  | 10 | 5 | 15 | 20 | 20 | 15 | 15 |  |  |  |  | 6.0 |  | 10 | 10 | 10 | 10 |  |  | 15 | 10 |
| ® Geropon HB | 7.5 |  |  |  |  |  |  |  |  |  |  |  | 7.5 | 6.0 | 10 |  |  |  |  |  |  |  |
| ® Degapas |  |  |  |  |  |  |  |  | 5 | 10 | 15 | 20 |  |  |  |  |  |  |  |  |  |  |
| ® Maranil | 4 | 2 | 2 | 2 | 2 | 4 | 3 | 0.1 | 2 | 3 | 4 | 1 | 3 | 2 | 1 | 2 | 2 | 2.0 | 4.0 |  | 4.0 | 4.0 |
| Antifreeze | 8 | 8 | 8 | 8 | 8 | 8 | 8 | 8 | 8 | 8 | 8 | 8 | 8 | 8 | 8 | 8 | 8 | 8 | 8 |  | 8 | 8 |
| ® Rhodopol 23 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.1 | 0.1 | 0.1 | 0.1 |  | 0.2 | 0.2 |
| ® Kobate C | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |  | 0.1 | 0.1 |
| Defoamer | 1 | 1 | 1 | 1 | 1 | 1 | 1 | 1 | 1 | 1 | 1 | 1 | 1 | 1 | 1 | 1 | 1 | 2.0 | 2.0 | *) | 1 | 1 |
| ® Darvan Nr. 3 | 1 | 1 | 1 | 1 | 1 | 1 | 1 | 1 | 1 | 1 | 1 | 1 | 1 | 1 | 1 | 1 | 1 | 1.0 | 1.0 |  | 1 | 1 |
| Isoproturon |  |  |  |  |  |  |  |  |  |  |  |  |  |  |  | 38.0 | 38 |  |  |  |  |  |
| Water to 100% |  |  |  |  |  |  |  |  |  |  |  |  |  |  |  |  |  |  |  |  |  |  |
| Analysis |  |  |  |  |  |  |  |  |  |  |  |  |  |  |  |  |  |  |  |  |  |  |
| Initial value | 23.4 | 26.9 |  |  | 25.5 |  |  |  |  |  |  |  | 23.6 |  |  |  |  | 1.49 | 1.51 | 1.60 | 24.3 | 22.7 |
| 3 months at 40° C. | 23.6 | 25.6 |  |  | 24.0 | 24.0 | 24.5 |  |  |  |  |  | 24.3 |  |  |  |  | 1.40 | 1.42 | 1.11 | 23.8 | 23 |
| 3 months at 50° C. | 21 |  |  |  | 23.7 | 20.5 | 22.0 |  |  |  |  |  | 21.5 |  |  |  |  | 0.4 | 0.49 | <0.1 |  |  |
| 3 months at RT |  | 26.7 |  |  |  |  |  |  |  |  |  |  |  |  |  |  |  |  |  |  |  |  |
| 14 months at RT |  |  |  |  |  |  |  |  |  |  |  |  |  |  |  |  |  |  |  |  |  | 23.2 |
| 5 months at RT |  |  |  |  |  |  |  |  |  |  |  |  |  |  |  |  |  | 1.47 | 1.46 |  |  |  |

*)See note above

The examples of Table 2 which follows are comparative examples in which surfactants, which are decisive as far as stability is concerned, from the class of the polyacrylates are exchanged for other, commercially available surfactants.

In contrast, the examples according to the invention listed in Table 1 show good stability values even after 3 months at 50° C. With an initial value of 22.7%, a value of 23.2%—within the analytical error margin—for Example 22 after 14 months at RT means no significant degradation.

TABLE 2

|  | 1a | 2a | 3a | 4a | 5a | 6a |
|---|---|---|---|---|---|---|
| Amidosulfuron | 35 | 45 | 45 | 45 | 45 | 45 |
| ® Orotan 850 |  | 6.0 |  |  |  |  |
| ® Berol 733 |  |  |  | 10 | 15 | 5 |
| ® Soprophor 3D33 |  | 3 |  |  |  |  |
| ® Genapol X 060 |  | 2 |  |  |  |  |
| ® Genapol X 080 | 1 |  | 1 | 1 |  |  |
| ® Vanisperse CB | 5 |  |  | 5 |  | 5 |
| ® Darvan No. 3 | 1 |  | 1 | 1 | 1 | 1 |
| Antifreeze | 8 | 8 | 8 | 8 | 8 | 8 |
| Thickener | 0.1 |  | 0.1 | 0.1 | 0.1 | 0.1 |
| Preservative |  |  |  |  |  |  |
| Defoamer | 1 | 1 | 1 | 1 | 1 | 1 |
| ® Borresperse 3A |  |  | 5 |  |  |  |
| ® Vanicell P |  |  |  |  | 5 |  |
| H₂O to 100 |  |  |  |  |  |  |
| Degradation after |  |  |  |  |  |  |
| 1 month at 50° C. | −5.5% | −6.2% | −5.1% |  | solid when ground | −7.8% |
| 2 months at 50° C. | −19.3% |  |  | −7.3% |  |  |
| 3 months at 50° C. | −21.4% |  |  |  |  |  |
| Stability | <3 months | <1 month | <1 month | <2 months |  | <1 month |

We claim:

1. An aqueous herbicidal preparation in the form of a suspension or suspoemulsion comprising 0.1–60% by weight of at least one herbicidal active substance from the sulfonylurea series, 0.5–20% by weight of at least one surfactant from the class of the alkali metal or ammonium salts of polyacrylic acid derivatives, 0.01–12% by weight of a dodecyl- or tridecylbenzenesulfonate, and 0–25% by weight of conventional adjuvants from the series of the wetting agents, dispersants, defoamers, thickeners, preservatives and antifreeze agents, and which preparation does not contain herbicidal active substances from the series of sulfonediamide derivatives.

2. A preparation as claimed in claim 1, comprising 1–45% by weight of at least one herbicidal active substance from the sulfonylurea series and 0.5–20% by weight of at least one polyacrylic acid derivative.

3. A preparation as claimed in claim 1, comprising 0.1–9% by weight of a dodecyl- or tridecylbenzenesulfonate and 0–15% by weight of conventional adjuvants from the series of the wetting agents, dispersants, defoamers, thickeners, preservatives and antifreeze agents.

4. The preparation as claimed in claim 1, which exists in the form of a suspension.

5. The preparation as claimed in claim 1, which exists in the form of a suspoemulsion.

6. A method of controlling undesired vegetation, which comprises applying to plants, seeds of plants or the area under cultivation an amount of a preparation as claimed in claim 1 which is sufficient for control.

* * * * *